United States Patent [19]

Jones

[11] Patent Number: 4,864,846
[45] Date of Patent: Sep. 12, 1989

[54] SELF-CLEANING POPPET VALVE FOR A CORE TESTING APPARATUS

[75] Inventor: Stanley C. Jones, Littleton, Colo.

[73] Assignee: Western Atlas International, Inc., Houston, Tex.

[21] Appl. No.: 259,523

[22] Filed: Oct. 17, 1988

[51] Int. Cl.⁴ .......................................... G01N 15/08
[52] U.S. Cl. ...................................................... 73/38
[58] Field of Search ...................................... 73/37, 38

[56] References Cited

U.S. PATENT DOCUMENTS

| | | | |
|---|---|---|---|
| 2,821,680 | 1/1958 | Slusser et al. | 73/38 |
| 3,638,478 | 2/1972 | Dietert et al. | 73/38 |
| 4,561,289 | 12/1985 | Jones | 73/38 |
| 4,643,099 | 2/1987 | Jones | 73/38 |
| 4,649,737 | 3/1987 | Jones | 73/38 |
| 4,671,100 | 6/1987 | Doussiet | 73/38 |

Primary Examiner—Hezron E. Williams
Attorney, Agent, or Firm—William A. Knox

[57] ABSTRACT

A poppet valve is mounted internally of a core tranfer piston of a core testing device. The valve face of the poppet valve is smoothly configured so that particulate matter will not cling thereto. A flow of gas is provided to blow debris away from the poppet valve assembly into the external environment.

5 Claims, 3 Drawing Sheets

SELF-CLEANING POPPET VALVE FOR A CORE TESTING APPARATUS

BACKGROUND OF THE INVENTION

1. Field of the Invention

This invention is concerned with apparatus for measuring the porosity and permeability of reservoir rock cores under simulated in-situ conditions. More specifically, the invention relates to equipment for automatic sequential testing of a plurality of rock core samples. Such equipment might be found in class 73/38.

2. Discussion of the Related Art

As is well known, hydrocarbon reserves are found in porous subsurface rock formations. Usually such formations are of marine sedimentary origin such as vugular limestone or dolomite and porous sandstone. Of interest in determining reservoir characteristics are porosity and permeability. Porosity is measured as the percentage of void space in the rock, available to contain fluids, relative to a unit of gross rock volume. Permeability is a measure of the ease with which fluids can migrate between the voids in the formation. Permeability is measured in millidarcys.

For purposes of this disclosure, porosity and permeability are measured using cylindrical plugs cut from the reservoir rock. Typically, the plugs are about one or one and one-half inches in diameter. A core sample is inserted into a core holder where it is subjected to axial and radial stress to simulate the stresses existing at the original formation burial depth.

Typically, the core holder is a cylindrical pressure vessel. A flexible sleeve or cuff is mounted inside the core holder to encase the core sample. After core insertion, the annular space between the inner wall of the core holder and the sleeve is pressurized to apply radial stress to the core sample. The applied pressure is comparable to the static stress existing at the formation depth which may range from 500 to 10,000 psi. The core holder has a porous fixed upper end plug against which the upper end of the core sample is pressed. A lower end plug, usually attached to a hydraulic piston or plunger, contacts the lower face of the core. The piston applies an axial stress to the core sample, commensurate with the applied radial stress. The upper and lower end plugs as well as the end faces of the core sample must be accurately perpendicular to the longitudinal axis of the core holder so that the core sample is evenly stressed.

The upper end plug usually includes an inlet valve through which an inert gas may be injected in the pressure range of 50-500 psig, in inverse proportion to the permeability. The face of the lower piston or plunger has a vent that can be releasably sealed by a poppet valve that is mounted inside the piston. To measure porosity, the vent in the lower plunger is sealed and a known volume of gas is injected into the core sample. To determine the permeability, the vent is opened so that the gas flow rate through the core sample can be measured.

This invention is related to U.S. Pat. Nos. 4,561,289, 4,643,019 and 4,649,737, issued respectively on 12/31/85, 02/17/87 and 03/17/87, all of which are incorporated herein by reference as showings of apparatus to which my present teachings may be applied as well as to provide a disclosure of prior art of which I am presently aware.

The '737 patent teaches an apparatus for automatically testing a plurality of core samples on a mass production basis. Essentially, that apparatus consists of a rotatable carousel having a plurality of storage carriers mounted thereon. In use, the carousel is rotated so that a selected core sample, in its storage carrier, is aligned with a core holder that is mounted above the carousel. A transfer piston then pushes the core sample from the storage carrier, up into the core holder for conducting the tests as previously described. Following the test procedure, the core sample is lowered from the core holder back into the carrier and another core sample is selected for test.

The '289 and '019 patents disclose a core-contacting disk that is press-fitted into the upper end of the transfer piston. The disk is either perforated or is made from a porous metal. Gas distribution channels are formed on the bottom of the perforated disk ('289) or on the top face of the transfer piston ('019).

I have encountered problems with the devices as taught by those patents.

Particularly with sandstones, the sand grains of many cores are poorly cemented. During the tests, sand grains, clay particles and dust break away, to fall through the vent in the transfer piston. The sand grains contaminate the O-rings of the poppet valve, possibly abrading the O-rings, creating a poor seal, that results in inaccurate porosity tests. If the porous metal disk as disclosed in the '019 patent is substituted for the perforated end plug as disclosed in the '289 and '737 patents, although gross contaminants are eliminated from the poppet valve, dust particles from friable core samples clog the micro-pores, preventing accurate permeability measurements. Frequent disassembly and cleaning of the apparatus seriously impeded core-testing production, which ideally approaches more than 350 such tests each day. Fine-mesh screens, mounted between the lower end cap and the end plug, have been tried but the screens either became clogged or were punctured by the particulate matter. The screens proved to be ineffective.

The disks disclosed by the aforementioned patents are press-fitted into the end of the transfer piston. The disks tended to become dislodged and to become skewed at an improper angle with respect to the longitudinal axis of the core holder. The effect damaged the end faces of the cores under test, again resulting in inaccuracies in test results.

SUMMARY OF THE INVENTION

It is an object of this invention to provide a self-cleaning poppet valve assembly for use with the transfer piston of an automatic core testing device and to provide a secure means for attaching an end plug or a disk to the upper end of the transfer piston.

In accordance with an aspect of this invention, I provide a transfer piston having upper and lower ends and having an internal passageway formed longitudinally therethrough. An internal inverted valve seat having an orifice is formed in the internal passageway at the upper end of the piston. A poppet valve assembly comprised of a second piston having upper and lower ends having a valve face formed at its upper end and a piston flange at its lower end, is slidably mounted in the internal passageway. The poppet valve is operable to selectively move the valve face in contact with the valve seat to close the orifice or away from the valve seat to open the orifice. Means are provided for positively flushing rock particles from the region around the valve seat and the valve face, into the internal passageway, where the debris is outwardly diverted to the external environment.

In another aspect of this invention, inner and outer gasket-retaining seats are formed around the upper end of the transfer piston. I provide a gasket-retaining washer and inner and outer gasket seals mounted between the washer and the gasket seats. A perforated end cap threadably engages, externally, the upper end of the transfer piston.

In another aspect of this invention, I provide an aperture in the transfer piston to provide communication between the internal passageway and the external environment. An upwardly-tapered concave bushing, having a bore for leakingly slidably receiving the piston portion of the poppet valve assembly, is fixedly mounted inside the internal passageway, just below the aperture but above the poppet valve piston flange, for outwardly directing rock particles passing through the internal passageway, out through the aperture and into the external environment.

BRIEF DESCRIPTION OF THE DRAWINGS

The advantages and benefits of this invention will be better appreciated by reference to the appended detailed description and the drawings wherein.

DETAILED DESCRIPTION OF THE PREFERRED EMBODIMENT

The automatic core testing apparatus to which this invention may be applied, is described in great detail in the aforementioned related patents. However, by way of review, the apparatus will be discussed here briefly with reference to the schematic drawings of FIGS. 1 and 2 which are intended merely to show the general operation of the apparatus. Novel features of this invention are displayed in FIGS. 3-5.

Figure 1:
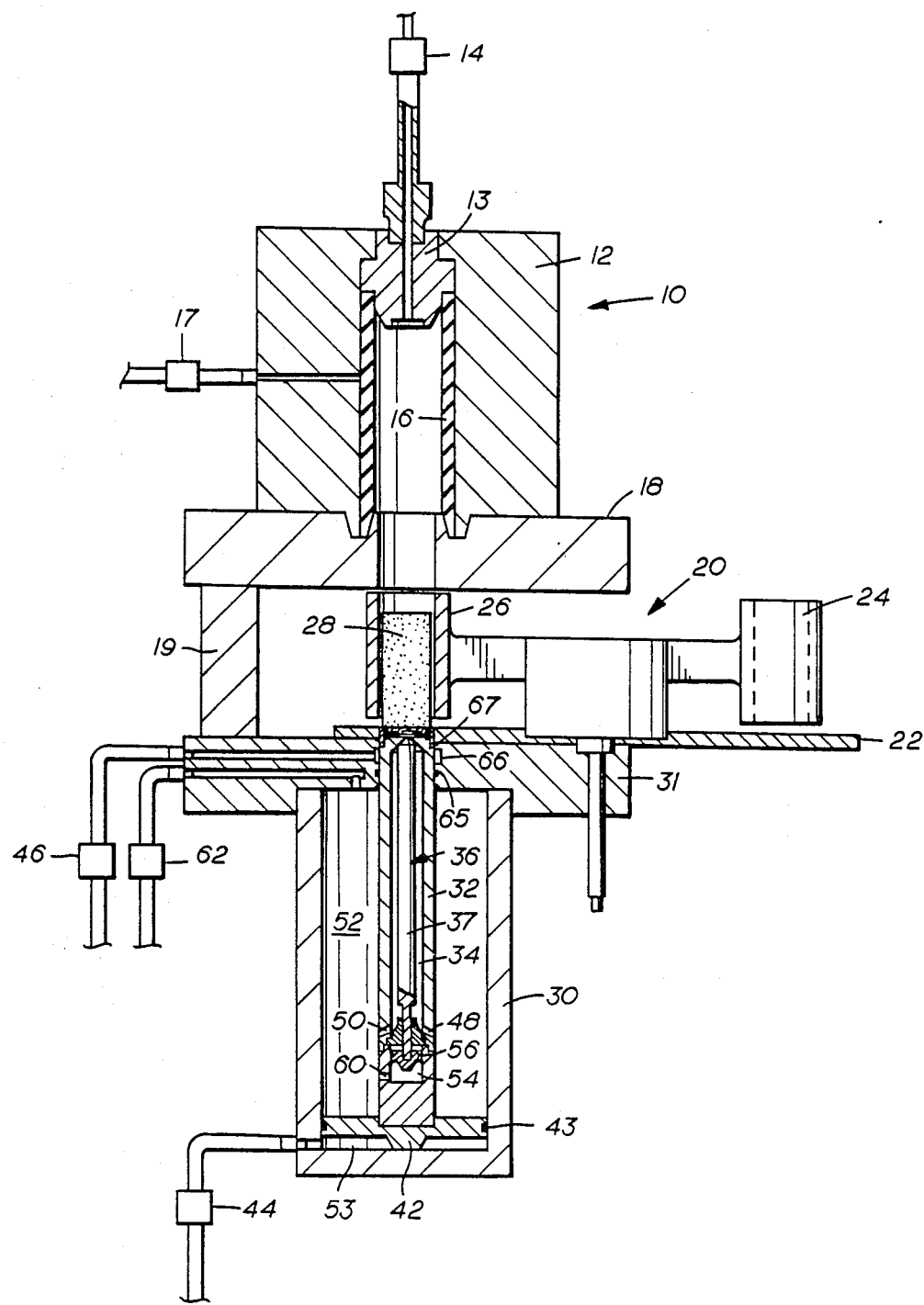
FIG. 1 is a schematic diagram of the apparatus with which this invention can be used.

FIG. 1 shows the core testing apparatus 10. It consists of a core holder 12 having an inert-gas inlet valve 14. A flexible Buna-N cuff or sleeve 16 is mounted inside core holder 12. A hydraulic inlet valve 17 is provided to admit hydraulic fluid to compress sleeve 16. Core holder 12 is mounted to flange 18 beneath which rotatable carousel 20 is mounted on a second flange 22. A bracket 19 is secured to flanges 18 and 22 by any convenient means. Carousel 20 supports a plurality of core storage carriers such as 24 and 26 for holding core samples such as 28. Two carriers are shown, but more may be used.

A cylinder 30, having a cover 31, fixed thereto by any convenient means, includes a core transfer piston 32. Transfer piston 32 has an internal passageway 34, wherein is mounted a poppet valve assembly 36, having a valve face 38 which opens and closes an orifice (not shown in FIG. 1) in an inverted valve seat 40 that is formed at the upper end of passageway 34 (see FIG. 3 for those details). Transfer piston 32 has a flange 42 at its lower end and an O-ring seal 43. A pressurized-gas inlet valve 44 is installed at the lower end of cylinder 30. Apertures 48 and 50 provide fluid communication between internal passageway 34 and the outside environment.

The poppet valve assembly 36 includes a piston rod 37, having upper and lower ends, that is mounted inside the internal passageway of transfer piston 32. Piston rod 37 has a piston flange 54 at its lower end which is sealed by an O-ring 56. An upwardly-tapered, concave bushing 58, having a bore 59 therethrough, is fixedly secured in internal passageway 34 for slidably receiving piston rod 37. The fit of piston rod 37 in bore 59 is snug but not tight so that air pressure will leak by to equalize the pressure above and below piston 54. The bushing 58 therefore leakingly and slidingly receives piston rod 37. Beneath flange 56, there is an air inlet 60 to the volume below piston 54. A vent valve 62 is provided to admit or exhaust air from the interior volume 52 of cylinder 30.

Figure 2:
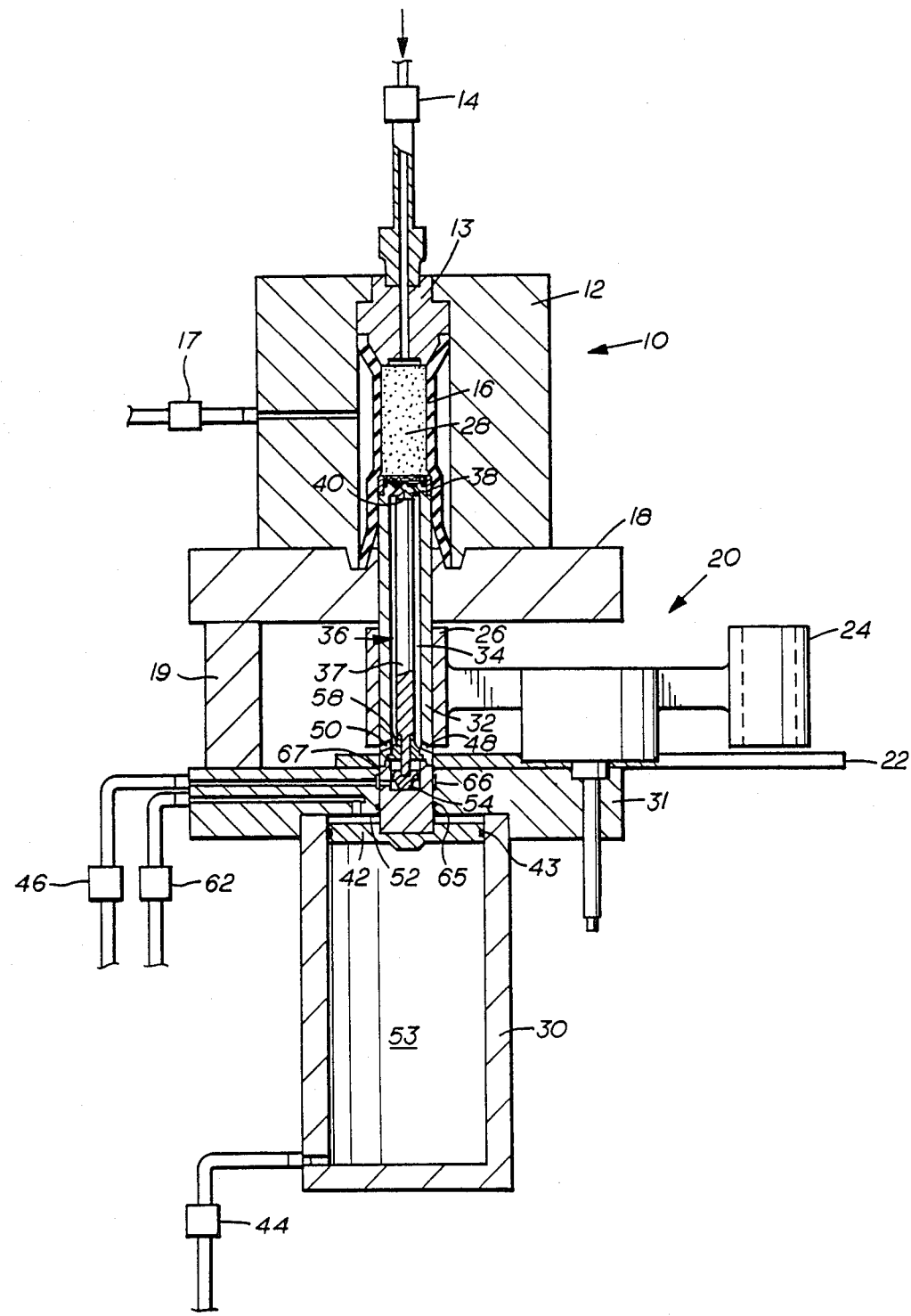
FIG. 2 is the apparatus of FIG. 1 with a core sample inserted into the core holder.

In operation, the carousel 20 is rotated to position a selected core sample above the core transfer piston 32. A gas, such as nitrogen, is admitted through valve 44 into cylinder 30 in the region 53 below flange 42. Core transfer piston 32 is forced upwards to push core sample 28 from its storage carrier 26 into sample holder 12 against upper end plug 13 as shown in FIG. 2. As transfer piston rises, air in volume 52 above the flange 42 is vented to the atmosphere through valve 62. Hydraulic fluid may now be admitted through valve 17 to compress sleeve 16 around core 28, as shown in FIG. 2, to apply a radial stress to the core sample. The pneumatic force acting against flange 42, applies the desired axial stress to the core sample.

When the transfer piston is raised as in FIG. 2, air inlet 60 is now exposed to volume 66 that is formed in cylinder cover 31 around piston 32. Volume 66 is sealed by O-rings 65 and 67. Air under pressure of about 125 psi is admitted through valve 46 to drive piston flange 54 of poppet valve assembly 36 upwards to close valve face 38 against seat 40.

Figure 4:
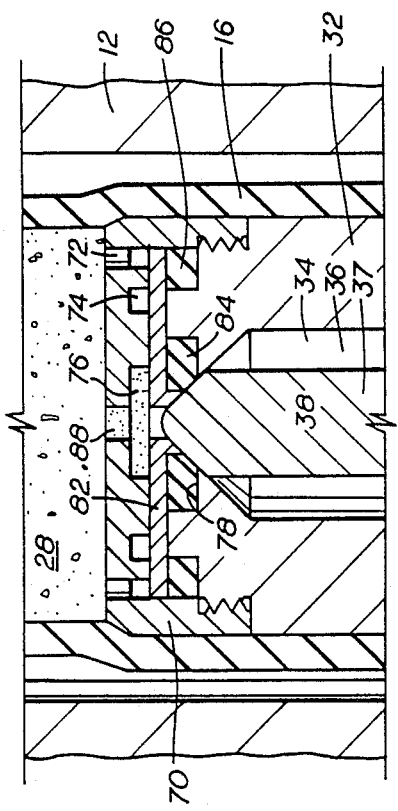
FIG. 4 is a detailed showing of the poppet valve assembly in the closed position.

With the poppet valve closed as shown in FIGS. 1 and 4, an inert gas, such as helium, is injected into the core sample to conduct a porosity test by the gas expansion method. Following the porosity test, core sample 28 is pressurized to about 240 psig with helium gas in preparation for the permeability test. The pressure below piston 54 is vented to the atmosphere through valve 46. Immediately thereafter, the volume 66 is evacuated to a pressure below atmospheric. Helium under pressure, acting against poppet valve piston rod 37, in conjuction with the pressure differential on either side of piston 54, forces the poppet valve assembly 36 to open. with the poppet valve now open, as shown in FIG. 2, a permeability test is conducted by measuring the rate of flow of the inert helium gas through the core sample 28, as well as the differential helium pressure across core sample 28. The flow of helium gas through the open poppet valve assembly into internal passageway 34 provides means for positively flushing rock particles from the region around valve face 38 and valve seat 40 into the external environment when the transfer piston is raised as shown.

Upon completion of the tests, the hydraulic pressure through valve 17 is released, and is evacuated to expand sleeve 16, the flow of helium gas is cut off at valve 14 and the pneumatic pressure applied through valve 44 is removed. Core transfer piston is then caused to retract and to return the core sample to its carrier by applying air pressure through valve 62 into region 52. Serendipitously, when air inlet 60 passes below O-ring 65, the air pressure in volume 52 causes poppet valve assembly 36 to close so that there will be no air leak through aperatures 48 and 50 and out the end of transfer piston 32 when those apertures are exposed to the air pressure in volume 52 as the piston 32 continues to retract.

Figure 3:
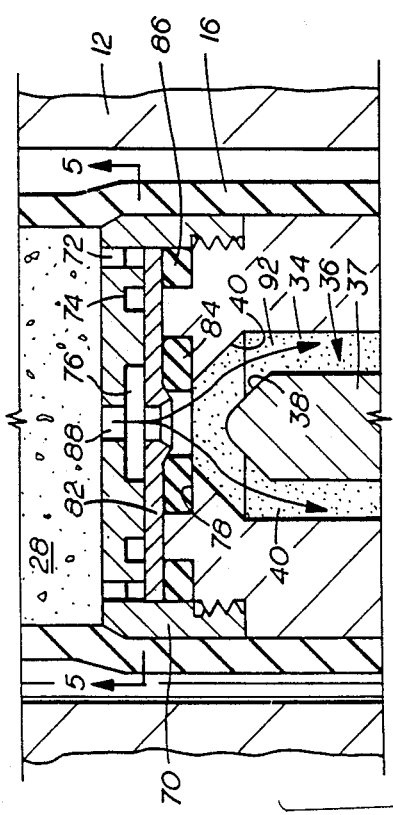
FIG. 3 is a detailed showing of the self-cleaning poppet valve assembly in the open position.
Figure 3:
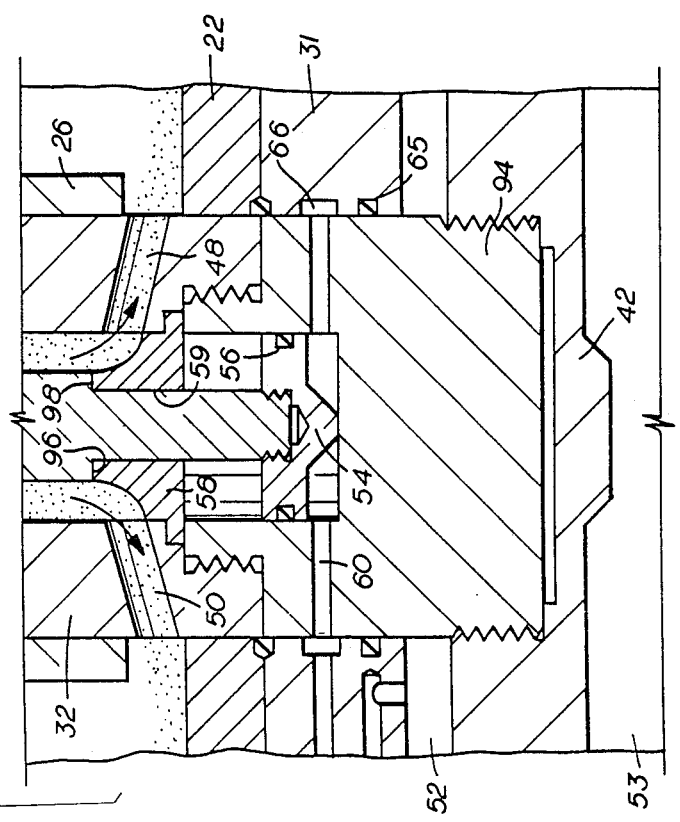

FIGS. 3 and 4 show in detail, the core transfer piston 32 and the poppet valve assembly 36 in the open and closed positions respectively. The figures are drawn to a somewhat exaggerated scale for the sake of clarity.

The upper portion of transfer piston 32 includes a perforated end cap 70 that threadedly engages the external wall of piston 32. End cap 70 (as seen from below along line 3—3' of FIG. 5) includes a plurality of perforations such as 72, circumferential grooves 74 and radial grooves 76 on its underside to distribute the inert helium gas evenly over the face of the core sample 28. Inner and outer gasket seats 78 and 80 are formed on the end of the piston member 32. A gasket-retaining washer 82, mounted beneath threaded end cap 70 holds inner and outer gaskets 84 and 86, respectively, which are O-rings, in their seats 78 and 80.

In FIG. 3, the poppet valve assembly is open. Gas flow through orifice 88 during a permeability test provides a positive draft represented by arrows 90 and 92 that flushes rock particles, represented by dots, by blowing them down through internal passageway 34. The particles are outwardly deflected by the upwardly tapered concave bushing 58 through slanted apertures 48 and 50 into the external environment. The poppet valve is thus self-cleaning.

The lower end of transfer piston 32 is closed by a threaded piston end cap 94. Threaded end cap 94 holds bushing 58 fixedly in place in interior passageway 34. Piston rod 37 is secured to piston flange 54 by any convenient means such as threadedly as shown. Piston rod 37 has an inverted shoulder 96 formed thereon that mates with a flat 98 at the top portion of bushing 58 when poppet valve assembly is open. That configuration prevents particulate matter from entering bore 59.

It is to be observed that the design of the valve face 38 of poppet valve assembly 36 is smooth so that there is no place for rock particles to cling thereto. Inner gasket 84 is arranged in its seat so that particles tend to fall away rather than to be entrapped between the gasket seat and the gasket as in the prior art, where the sealing O-ring was contained in a groove in the conical face of rod 37.

FIG. 4 shows the poppet valve assembly to be closed wherein the valve face contacts the inverted valve seat 40 that is formed at the upper end of the internal passageway 34 to close orifice 88 which is sealed by lower gasket 84 by the force applied to it from pneumatic pressure applied to piston 54.

Figure 5:
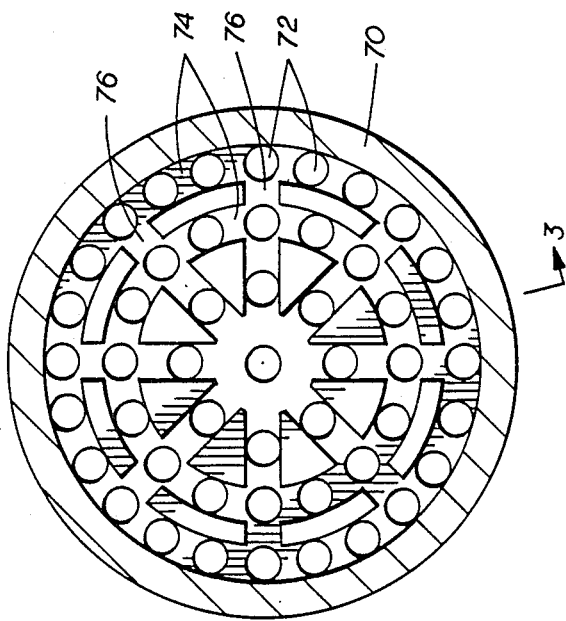
FIG. 5 shows the arrangement of the perforations and fluid distribution channels of the end cap taken along lines 5—5' of FIG. 3.

FIG. 5 shows the arrangement of the perforations 72, the circumferential gas-distributing grooves 74 and the radial gas distribution grooves 76 in end cap 70, taken along line 5—5' of FIG. 3.

Those skilled in the art will recognize that many variations in the design of this invention are possible, but which will fall within the scope and spirit of this disclosure which is limited only by the apended claims.

I claim as my invention:

1. A self-cleaning poppet-valve assembly for use with an automatic testing apparatus for measuring characteristics of a reservoir rock core sample under simulated in-situ conditions, comprising:

a core transfer piston having upper and lower ends and an internal passageway, operatively extendable to axially move a core sample to a core sample holder and for applying an axial stress to said core sample;

an internal inverted valve seat having an orifice formed in said internal passageway at the upper end of said core transfer piston;

a poppet valve including a piston rod having upper and lower ends, a valve face formed at the upper end thereof and a piston flange at its lower end mounted within the internal passageway of said transfer piston, said poppet valve being operable to selectively move said valve face to a valve-seat contacting position to close said orifice and away from said valve seat to open said orifice;

means for positively flushing away rock particles from the region around said valve seat and said valve face when said poppet valve moves to open said orifice;

inner and outer gasket-retaining seats formed at the upper end of said transfer piston;

a gasket-retaining washer;

inner and outer gaskets positioned respectively between said inner and outer gasket seats and said gasket-retaining washer; and a perforated core-contacting end cap threadedly engaging externally, the upper end of said transfer piston, to secure said gasket-retaining washer and said inner and outer gaskets to the upper end of the transfer piston.

2. The self-cleaning poppet valve assembly as defined by claim 1, further comprising;

at least one aperture in the wall of said transfer piston to provide communication between said internal passageway and an external environment;

means, mounted within said internal passageway, associated with the piston rod of said poppet valve assembly, mounted beneath said aperture for outwardly directing the flushed-away rock particles from said internal passageway, into said external environment through said aperture when said transfer piston is extended.

3. The self-cleaning poppet valve assembly as defined by claim 2 wherein said means for outwardly-directing comprises:

an upwardly-tapered concave bushing fixedly secured in said internal passageway, beneath said aperture, said upwardly-tapered concave bushing including a central bore for leakedly slidingly receiving the piston rod of said poppet valve assembly.

4. The self-cleaning poppet valve assembly as defined by claim 3 wherein said means for positively flushing comprises:

means for opening said orifice after axial stress is applied to said core sample;

means for directing a flow of pressurized gas through said core sample and through the open orifice thereby to blow rock particles from said region around said valve seat and said valve face, through said internal passageway and out into the external environment through said at least one aperture.

5. The self-cleaning poppet valve assembly as defined by claim 3 comprising:

a flat on the top of said upwardly-tapered concave bushing; and an inverted shoulder formed on said piston rod for mating with said flat when said orifice is open.

* * * * *